United States Patent [19]
Monget

[11] Patent Number: 5,180,555
[45] Date of Patent: Jan. 19, 1993

[54] MICROBIOLOGICAL ANALYSIS CUP OR THE LIKE

[75] Inventor: Daniel Monget, Lagnieu, France

[73] Assignee: Bio Merieux, Marcy l'Etoile, France

[21] Appl. No.: 602,895

[22] Filed: Oct. 25, 1990

Related U.S. Application Data

[63] Continuation of Ser. No. 313,195, Feb. 16, 1989, abandoned.

[30] Foreign Application Priority Data

Feb. 16, 1988 [FR] France ............................... 88 02180

[51] Int. Cl.$^5$ ............................................. G01N 21/03
[52] U.S. Cl. ................................... 422/102; 436/165; 436/809; 435/299; 435/301; 356/246
[58] Field of Search ............... 422/102; 436/165, 809; 435/299-301, 284, 287; 356/244, 246

[56] References Cited

U.S. PATENT DOCUMENTS

| | | | |
|---|---|---|---|
| 3,190,731 | 6/1965 | Weiskopf | 422/102 |
| 3,432,275 | 3/1969 | Unger | 422/102 |
| 3,480,399 | 11/1969 | Hamilton | 422/102 |
| 4,303,616 | 12/1981 | Kano et al. | 422/102 |
| 4,357,301 | 11/1982 | Cassaday et al. | 422/102 X |
| 4,466,740 | 8/1984 | Kano et al. | 356/246 |
| 4,661,460 | 4/1987 | Sakuma | 422/73 X |

Primary Examiner—Lynn M. Kummert
Attorney, Agent, or Firm—Browdy and Neimark

[57] ABSTRACT

A microbiological analysis cup having a flat bottom, a wall with a circular section connected to this flat bottom and an open end. Moving from the flat bottom wall of the cup, there are at least three superposed tapered zones whose respective base diameters increase from the flat bottom to the open end.

The cup makes it possible to work with very small volumes of bacterial suspension for short incubation periods, which makes it very economical to use.

5 Claims, 1 Drawing Sheet

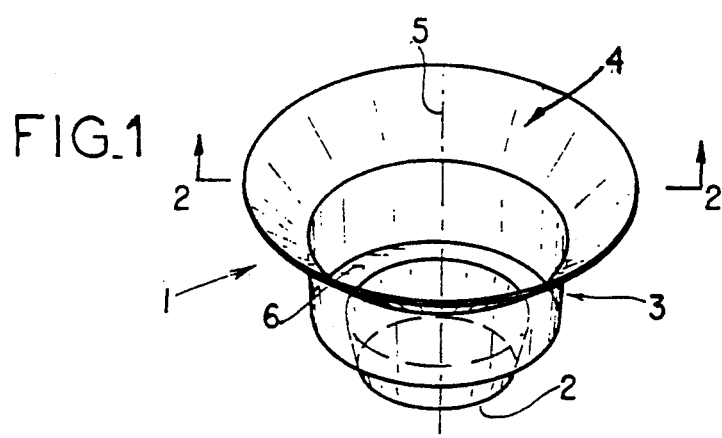
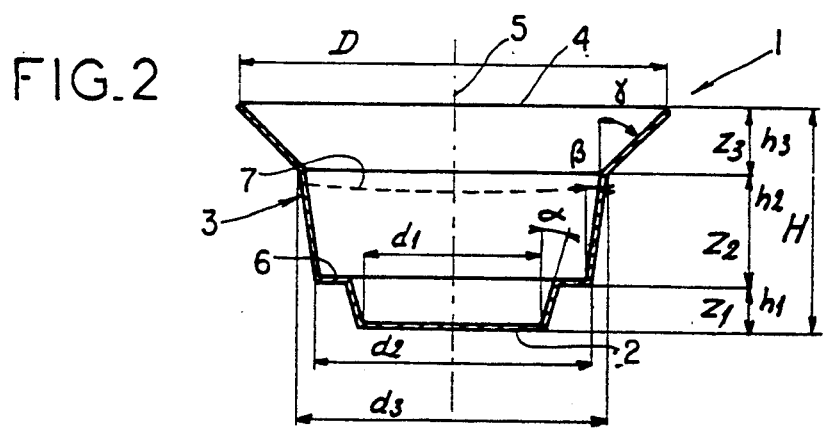
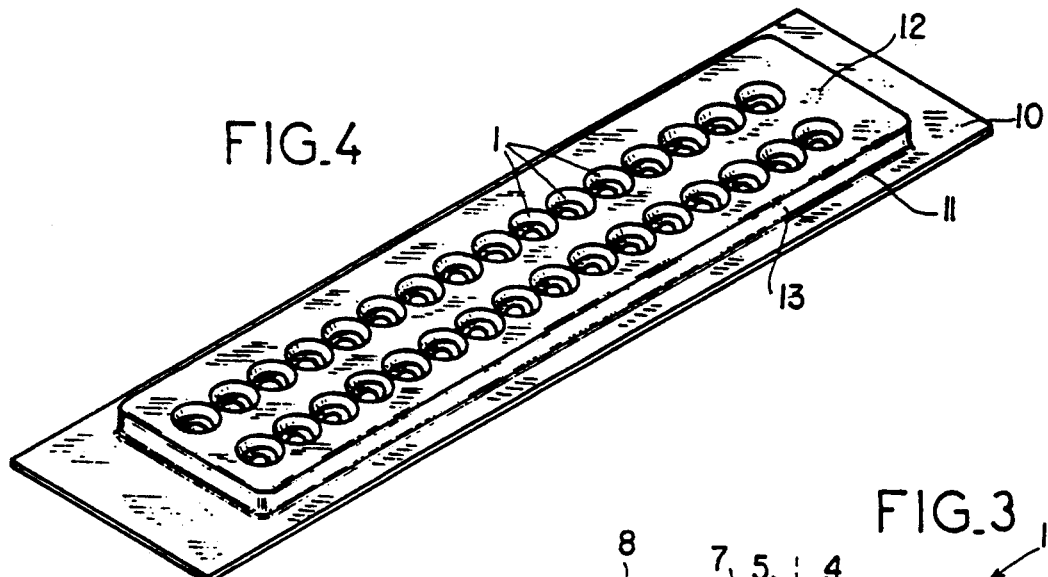
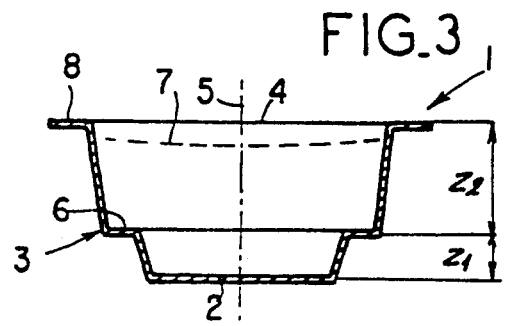

MICROBIOLOGICAL ANALYSIS CUP OR THE LIKE

This application is a continuation of application Ser. No. 07/313,195 filed Feb. 16, 1989, now abandoned.

FIELD OF THE INVENTION

This invention relates to a microbiological analysis cup or the like comprising a flat bottom, a wall with a circular section connected to this flat bottom and an open end.

BACKGROUND OF THE INVENTION

Such a type of cup is used in some analysis methods, particularly for rapid diagnosis by identification, or determination of sensitivity to antibiotics (antibiogram) for a given bacterial strain. These methods are already used in a standardized way in some laboratories, with the help of thermoformed, synthetic rectangular plates, exhibiting an elongated shape and each provided with one or two rows of small tapered cups with a flat bottom constituting miniaturized test tubes. Each of the cups is initially filled either with a different dehydrated growth substrate associated with a suitable chemical indicator of consumption of the substrate or with the same dehydrated antibiotic in different concentrations or a different dehydrated antibiotic.

These methods then involve a seeding or inoculation operation by introduction of a given volume of aqueous suspension of a microbial strain in each cup. Following this operation, the cups are put into an oven for a growth phase which lasts twenty four hours.

Within the context of a bacterial identification, the consumption of the substrate belonging to each cup by the strain is displayed by the chemical indicator which changes the coloring of the culture medium contained in the cup. Reading the colorings of the different cups is performed visually and preferably automatically by a photometer equipped with a filter changer measuring the light transmitted by the suspension. The use by the unknown strain of the different substrates of the cups of the plate makes possible the biochemical identification of the strain.

Within the context of determination of the sensitivity of a given strain to antibiotics, the results are read by a photometer measuring, by turbidity, the ratio of the diffused light to the light transmitted by the suspension. The turbidity is maximum, when the strain considered is insensitive to the antibiotic tested and develops normally in the culture medium.

The photometers used in both cases comprise a light source located above the cup concerned emitting an incident light beam perpendicular to the flat bottom of the cup and three receiving diodes one of which, measuring the transmitted light, is placed directly below the flat bottom, the other two diodes measuring the diffused light and each offset about 30° relative to the one measuring the transmitted light are placed opposite the wall of the tapered cup considered.

In a first embodiment now known, the analysis cups exhibit a flat bottom connected to a lateral wall giving them a tapered configuration. In regard to their dimensions, they have a considerable base diameter and a slight height. The volume of suspension contained in each of them is about 135 microliters and the necessary incubation period in the oven is twenty four hours. This considerable period is harmful to the economical profitability of this type of microbiological analysis.

With this taken into consideration, it was imagined in a known second embodiment to reduce the diameter of these tapered cups. Thus, the optical path traveled by the incident light ray of the photometer through the bacterial suspension, for the same volume of 135 microliters, is longer, which has the effect of increasing the sensitivity of the reading photometer and therefore of making possible reliable optical measurements on bacterial suspensions with a slight growth period, more precisely four hours, for which the indication of the considered reactions is still only incipient.

However, it should be noted that the volume of bacterial suspension contained in each of these cups remains high, on the order of 135 microliters. Now, identification racks of strains and antigram can require up to thirty two cups, which is equivalent to a considerable volume of bacterial suspension (about six milliliters with the dead volume) and therefore to a high number of colonies necessary to obtain the suspension.

Further, it is known that during the microbiological analysis, the number of isolated bacterial colonies to be sampled should be as small as possible. This is due, on the one hand, to the limited number of colonies available for a given germ and, on the one hand, to the risk of bacterial mixing during the sampling. Still the level of germs should be sufficient to obtain a standard opacity of the suspensions, essential to guarantee precise results for the reading.

It is clear that considerable volumes of bacterial suspension per cup are completely incompatible with the constraints of practice.

With this taken into account, it therefore was necessary to develop an analysis cup containing a small volume of bacterial suspension and offering a relatively long optical path to the incident light ray of the photometer to reduce the period of the incubation phase to four hours.

The technical problem then encountered was linked to the surface tension phenomena of the suspension. Actually, a very small volume of suspension introduced into a cup is in the form of a droplet whose cohesion is very great and which, consequently exactly fits, with difficulty, the shape defined by the wall and bottom of known tapered cups. Consequently, the droplet can be fixed in different positions on the wall of the cup because of slight wettability of the latter.

Its meniscus therefore is practically never approximately in a plane parallel to the bottom of the cup. Further, even with the most favorable hypothesis of positioning of the meniscus, the latter is unstable and constantly evolves from a concave shape to a convex shape and vice versa.

Thus, the results obtained during colorimetric or turbidimetric reading through such cups are inexact and false. Further, the reproducibility of the results obtained is absolutely not assured. To this is added the fact that the variability of the shape of the meniscus from one cup to the next runs the risk of falsifying the overall result of the analysis.

SUMMARY OF THE INVENTION

In view of these problems, the applicant engaged in thorough research and numerous tests which made it possible to arrive at a cup entirely original in its shape, making it possible to eliminate said drawbacks and lacunae, able to guarantee reliable, reproducible measurements for correct microbiological analyses and requiring only a small volume of bacterial suspension and a short incubation period.

For this purpose, the microbiological analysis cup or the like, which is the object of the invention, is of the type comprising a flat bottom, a wall with circular section connected to a flat bottom and an open end, is characterized in that going from the flat bottom the wall of the cup exhibits at least two superposed tapered zones $Z_1$ and $Z_2$, whose respective base diameters increase from the flat bottom to the open end, and in that the first tapered zone $Z_1$ of the cup comprising the flat bottom is connected to the second tapered zone $Z_2$ by an annular rim in a plane parallel to the flat bottom whose outside diameter corresponds to the base diameter of second tapered zone $Z_2$ of the cup.

In this cup, the meniscus obtained for small volumes of bacterial suspension is relatively flat, i.e., approximately parallel to the bottom of the cup. The annular rim of the cup assures a good seating of the meniscus and thus guarantees its stability in time, making it possible a good precision and a good reproducibility of the photometric measurements.

In a preferred embodiment, this cup comprises a flared tapered zone $Z_3$ connected to the second tapered zone $Z_2$ and extending the latter to the open end, the base diameter of this third tapered zone $Z_3$ corresponding to the upper diameter of this second tapered zone $Z_2$.

According to a nonlimiting example and interesting example, the heights of the first tapered zone $Z_1$, of the second tapered zone $Z_2$ and the third tapered zone $Z_3$ are respectively on the order of 20%, 50% and 30% of the total height of the cup, while the base diameter of first tapered zone $Z_1$, the difference between the outside diameter and the inside diameter of the annular rim and the base diameter of the third tapered zone $Z_3$ have lengths respectively equal to about 43%, 7% and 69% of the upper diameter of the third tapered zone.

The considerable flaring constituted by the third tapered zone of the cup facilitates the introduction of the bacterial suspension and reagents, allows placing of oil or paraffin to make the medium anaerobic and, finally, favors the centering of the cups when they are stacked on one another for storage or packaging or when they are put on the support of the photometer. Further, because of concentration of colors on a reduced surface delimited by second tapered zone $Z_2$, the visual reading of the colored reactions is made easier. To facilitate removal of the cup from the mold during its production, the angle of inclination of the wall in tapered zone $Z_1$ relative to a plane perpendicular to the plane comprising the flat bottom is greater than that of the wall in tapered zone $Z_2$ and less than that of the wall in tapered zone $Z_3$.

According to another embodiment of the invention, the cup exhibits a second tapered zone $Z_2$ extended outward to the level of its open end by an annular flange in a plane parallel to the flat bottom.

This invention also relates to an elongated rectangular plate able to be used as a support for the cups, and whose upper plane is connected to the edges of the open ends of the cups which it comprises.

BRIEF DESCRIPTION OF THE DRAWINGS

In any case, the invention will be better understood with the help of the following description, with reference to the accompanying diagrammatic drawing representing by way of nonlimiting examples two embodiments of this microbiological analysis cup or the like:

FIG. 1 is a perspective view of the cup according to the invention;

FIG. 2 is a view in diametral section along 2—2 of FIG. 1;

FIG. 3 is a view in diametral section of another embodiment of this cup;

FIG. 4 is a perspective view of a microbiological analysis plate or the like, comprising cups according to the invention.

DETAILED DESCRIPTION OF THE INVENTION

Cup 1 represented in FIGS. 1 and 2 is a container comprising a flat bottom 2, a wall 3 and an open end 4. Its configuration is symmetrical relative to its median axis 5.

Wall 3 has a circular cross section. As FIG. 2 shows, it exhibits, going from flat bottom 2, three tapered zones first $Z_1$, $Z_2$, $Z_3$ of different dimensions. Their respective base diameters $d_1$, $d_2$ and $d_3$ increase from flat bottom 2 to open end 4.

First tapered zone $Z_1$ of wall 3 is connected to second tapered zone $Z_2$ by a flat annular rim 6 in a plane parallel to flat bottom 2. The outside diameter of this annular rim 6 corresponds to base diameter $d_2$ of second tapered zone $Z_2$ of wall 3.

This second tapered zone $Z_2$ is connected to flared third tapered zone $Z_3$ which extends to the open end 4 of cup 1. Base diameter $d_3$ of this third tapered zone $Z_3$ corresponds to the upper diameter of this second tapered zone $Z_2$.

Wall 3 at the level of first tapered zone $Z_1$ forms angle $\alpha$ with a plane perpendicular to flat bottom 2 of a value greater than that of an angle $\beta$ existing between wall 3 at the level of second tapered zone $Z_2$ and a vertical plane perpendicular to annular rim 6 and less than that of an angle $\alpha$ formed between a vertical plane perpendicular to that comprising flat bottom 2 and wall 3 in third tapered zone $Z_3$.

Meniscus 7 of the bacterial suspension represented in a dotted line in FIG. 2 is relatively flat and parallel to flat bottom 2 because of annular rim 6 which assures its seating and because of the different inclinations of wall 3 in tapered zones $Z_1$, $Z_2$, $Z_3$ relative to the vertical.

By way of illustrative nonlimiting example, the relative dimensions of the different tapered zones of wall 3 and cup 1 have been determined as follows: the total height of cup 1 being designated by H, heights $h_1$, $h_2$, $h_3$ of corresponding tapered zones $Z_1$, $Z_2$, $Z_3$ respectively about 21%, 48% and 31% of the total height H of cup 1.

Relative to the diameters of the different zones $Z_1$, $Z_2$, $Z_3$, if upper diameter D of third tapered zone $Z_3$ is considered, i.e., open end 4, base diameter $d_1$ of first tapered zone $Z_1$ has a length representing about 45% of that of D, the difference between outside diameter $d_2$ and the inside diameter of annular rim 6 has a length representing about 7% of that of D and finally base diameter $d_3$ of the third tapered zone has a length representing about 69% of that of D.

More precisely, the cup according to the invention can exhibit the following dimensions:

$H \simeq 5$ mm $\pm 2$ mm $\quad D \simeq 9.5$ mm
$h_1 \simeq 1$ mm $\quad d_1 \simeq 4.1$ mm
$h_2 \simeq 2.5$ mm $\quad d_2 \simeq 6$ mm
$h_3 \simeq 1.5$ mm $\quad d_3 \simeq 6.6$ mm The volume contained per cup can vary, in this example, from 50 to 60 microliters.

For the different capacities per cup, the dimensions vary according to the standards defined above.

Another embodiment of the invention is represented in FIG. 3 of the drawing in which the same elements will be designated by the same references as above. Cup 1 considered also comprises a flat bottom 2 connected to a wall 3 with a circular cross section ending in on open end 4. Cup 1 is symmetrical relative to median axis 5.

Going from flat bottom 2, wall 3 exhibits only two tapered zones $Z_1$, $Z_2$ connected to one another by an annular rim 6 in a plane parallel to flat bottom 2 and identical in their shapes and dimensions relative to those described above for the cup according to the preferred embodiment.

The upper edge of second tapered zone $Z_2$ delimiting open end 4 of cup 1 is extended by an annular rim 8 directed outward of cup 1 and in a plane parallel to flat bottom 2. This annular rim 8 constitutes a break in the level of second tapered zone $Z_2$ of wall 3 stabilizing meniscus 7 of the bacterial suspension contained in the two tapered zones $Z_1$ and $Z_2$ of wall 3 of cup 1.

It should be pointed out that the cups according to the invention are obtained particularly by thermoforming of a synthetic material.

A cup support plate, like that represented in FIG. 4, is advantageously provided for using the cup. Plate 10 exhibits an elongated rectangular shape. It is delimited by edges 11 forming a support part. These edges 11 are connected to upper plane 12 of plate 10 by walls 13 perpendicular to the latter. Upper plane 12 is parallel to the plane comprising support edges 11 and is connected to the edges of the open ends of cups 1 according to the invention, grouped in rows, the number of cups 1 represented in FIG. 4 not being limiting. These support plates 10 of microbiological analysis cup 1 are obtained in a standard way by thermoforming of a suitable synthetic material.

Of course, the invention is not limited to the example described; rather, it takes in all embodiments that are equivalent and based on the same principle.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A microbiological cup for optical sensing, said cup including a reactive medium, said cup further including means to receive a quantity of an aqueous suspension of a microorganism, said cup having a flat bottom, a wall having a circular cross-section and an open top having an upper diameter, the improvement comprising:

the wall of said cup comprises three superimposed tapered zones, said tapered zones having respective different inclinations, said three tapered zones including a first lower tapered zone, a second higher tapered zone, and a third top tapered zone which extends to the open top of said cup, wherein base diameters of each of said three tapered zones increase from the flat bottom to the open top of said cup;

said first tapered zone extends from the flat bottom of said cup and an upper end thereof is connected to a lower end of said second tapered zone by an annular rim lying in a plane parallel to the plane of said flat bottom;

said second tapered zone extends from said annular rim and an upper end thereof is connected at an angle to a lower end of said third tapered zone, wherein the angle is constructed so as to restrict the rise of liquid sample therein due to capillary action.

2. A cup according to claim 1 wherein the height of said first tapered zone is less than the height of said second tapered zone.

3. A cup according to claim 1 wherein said annular rim has an inside diameter and an outside diameter and the difference between the outside diameter and the inside diameter of said annular rim is around 7% of the upper diameter of the open top of said cup.

4. A cup according to claim 1 wherein the angle of inclination of said first tapered zone relative to the plane of the flat bottom of said cup is greater than the angle of inclination of the wall of said third tapered zone relative to the plane of the flat bottom.

5. A microbiological analysis plate comprising a plurality of aligned and spaced cups, each of said cups including a reactive medium, each of said cups further including means to receive a quantity of a liquid sample comprising an aqueous suspension of a microorganism, wherein the wall of each cup comprises three superposed tapered zones, said three tapered zones having respectively different base diameters and inclinations, including a first lower zone, a second higher zone and a third highest zone, each of said three zones having an upper border and a lower border, the base diameters of each of said three zones increasing from the flat bottom to the open top of each of said cups; wherein said first zone extends from the flat bottom of said cup and the upper border thereof is connected to the lower border of said second zone by a horizontal annular rim; said third zone extends from said second zone to the open top of said cup such that the lower border of said third zone is the upper border of said second zone; wherein said horizontal annular rim lies in a plane parallel to the plane of said flat bottom, so as to seat the meniscus of sample liquid contained in each of said cups on said annular rim;

and wherein said second tapered zone extends from the annular rim and is connected at an angle to the lower border of said a third tapered zone, wherein the angle is constructed so as to restrict the rise of sample liquid therein due to capillary action.

* * * * *